(12) United States Patent
Plicchi et al.

(10) Patent No.: US 7,664,547 B2
(45) Date of Patent: Feb. 16, 2010

(54) ACTIVE IMPLANTABLE MEDICAL DEVICE WITH BIVENTRICULAR PACING AND AUTOMATIC OPTIMIZATION OF PACING CONFIGURATION

(75) Inventors: Gianni Plicchi, Bologna (IT); Emanuela Marcelli, Macerata (IT); Fabrizio Renesto, Borgofranco d'Ivrea (IT)

(73) Assignee: Ela Medical S.A.S., Montrouge (FR)

( * ) Notice: Subject to any disclaimer, the term of this patent is extended or adjusted under 35 U.S.C. 154(b) by 456 days.

(21) Appl. No.: 11/425,668

(22) Filed: Jun. 21, 2006

(65) Prior Publication Data
US 2006/0293715 A1 Dec. 28, 2006

(30) Foreign Application Priority Data
Jun. 22, 2005 (FR) .................................. 05 06317

(51) Int. Cl.
*A61N 1/00* (2006.01)
(52) U.S. Cl. .......................................................... 607/9
(58) Field of Classification Search ...................... 607/9, 607/17, 24, 27
See application file for complete search history.

(56) References Cited
U.S. PATENT DOCUMENTS 5,304,208 A 4/1994 Inguaggiato et al.
5,496,351 A 3/1996 Plicchi et al.
6,253,106 B1 6/2001 Legay et al.
6,556,866 B2 4/2003 Dal Molin et al.
7,079,896 B1* 7/2006 Park et al. ...................... 607/17
7,139,609 B1* 11/2006 Min et al. ...................... 607/17
2002/0151938 A1* 10/2002 Corbucci ...................... 607/25
2003/0208240 A1 11/2003 Pastore et al.
2004/0054381 A1 3/2004 Pastore et al.
2004/0158293 A1* 8/2004 Yonce et al. .................... 607/9
2005/0027320 A1 2/2005 Nehls et al.

FOREIGN PATENT DOCUMENTS

| EP | 515319 | 11/1992 |
| EP | 655260 | 5/1995 |
| EP | 925806 | 6/1999 |
| EP | 1108446 | 6/2001 |
| WO | WO2005/011803 | 2/2005 |

* cited by examiner

*Primary Examiner*—George Manuel
(74) *Attorney, Agent, or Firm*—Orrick Herrington & Sutcliffe, LLP

(57) ABSTRACT

An active implantable medical device with biventricular pacing and automatic optimization of pacing configuration. The device collects and analyzes an endocardial acceleration signal (EA), and searches for an optimal pacing configuration based upon a performance index derived from at least one value relating to one and/or the other of the two endocardial acceleration peaks (PEA I, PEA II) over a given heart cycle. Optimization search operates through a scanning of a parameter, e.g., atrio-ventricular delay, and calculation of the surface area underneath the characteristic of the peak amplitude as a function of the scanned parameter (atrioventricular delay).

19 Claims, 1 Drawing Sheet

ACTIVE IMPLANTABLE MEDICAL DEVICE WITH BIVENTRICULAR PACING AND AUTOMATIC OPTIMIZATION OF PACING CONFIGURATION

FIELD OF THE INVENTION

The present invention relates to "active implantable medical devices" as such Devices are defined by the Jun. 20, 1990 Directive 90/385/CEE of the Counsel of the European Community, and more particularly to pacemakers, defibrillators and/or cardioverter devices that are able to monitor heart activity and to deliver to the heart electrical pulses intended for pacing, resynchronization, cardioversion and/or defibrillation in response to a diagnosis of a cardiac rhythm disorder. This invention is more particularly applicable to such devices that are able to provide permanent pacing of both right and left ventricles, so as to resynchronize them, which technique is commonly referred to as "CRT" (Cardiac Resynchronization Therapy) or "BVP" (Bi-Ventricular Pacing).

BACKGROUND OF THE INVENTION

As an alternative or as an addition to the treatment of heart rhythm disorders, it has been proposed that certain troubles of myocardial contraction observed in patients with heart failure be treated by biventricular pacing, whether the troubles are spontaneous or induced by traditional pacing. Reference is made to the study by J. C. Daubert et al., published in *Stimucoeur*, 25, n°3, on pages 170-176, which presents a summary on the studies made on that topic. This CRT therapy has allowed one to observe most of time astonishing results for patients with class III heart failure, who are not improved by usual treatments.

One such CRT pacemaker is for example described in European Pat. EP-1 108 446 and its counterpart U.S. Pat. No. 6,566,866 (commonly assigned herewith to ELA Medical), which disclose a device allowing to apply a variable interventricular delay between two ventricular pacing pulses, adjusted so as to resynchronize contraction of the ventricles, with a fine optimization of the patient's hemodynamic status.

Most of the CRT devices used nowadays are so-called "mutisite" prostheses, in which the electrodes are positioned in a plurality of distinct respective sites, comprising at least one atrial site in addition to left and right ventricular sites, as in "triple-chamber" prostheses (dual ventricular pacing and right atrial sensing/pacing) or "quadruple chamber" prostheses (dual ventricular pacing and dual atrial sensing/pacing).

The physical location of endocardial electrodes in relation with myocardial tissue will be hereinafter referred to as "pacing sites"; usually, these sites can only be chosen during the implantation procedure, through an appropriate positioning of electrodes. It is important to make sure of the efficacy of the chosen sites, because of the potential influence, with a long term perspective, on the resynchronization therapy. In some cases, the multisite device has plural electrodes placed in the same cavity, giving one an opportunity to modify the pacing site in that cavity, by internal commutations of the device between said electrodes.

Hereinafter, reference to "pacing sequence" is to firstly, the order along which the pacing pulses are delivered to the heart (for example: first the atrium, then left ventricle, then right ventricle), and secondly, the time intervals separating delivery of those successive pulses. The pacing sequence is parameterized during the implantation procedure, and may further be modified, if need be, through appropriate internal commutations of the device and adjusting the parameters of pulse sequencing.

Hereinafter, reference to "pacing configuration" is to the combination of the characteristics relating to "pacing sites" and those relating to "pacing sequence".

The invention is proposing a solution to the problem, as recognized by the inventors, of optimizing biventricular pacing through selection of the most appropriate pacing sites and the best sequence for pacing these sites. This optimizing is of course performed during the implantation procedure, but may advantageously be performed again at periodic or aperiodic intervals, in order to follow up the course of the patient's general hemodynamic status, particularly during phases of improvement or degredation of the condition of the myocardium.

There are currently existing various means for assessing the degree of efficacy of biventricular pacing. Most of them consist of echographic techniques, which always have to be performed by qualified personnel in hospital environment. For that reason they are costly, and cannot be utilized as often as it could be useful or necessary, without interfering with the patient's daily life.

EP-1 108 446 and U.S. Pat. No. 6,566,866 referred to above propose a solution that consists of assessing the degree of synchronization of left and right ventricles contractions, through measurement of intracardiac bioimpedance, data representative of cardiac output and therefore ejection fraction, considered as being the reference hemodynamic parameter.

OBJECTS AND SUMMARY OF THE INVENTION

The present invention, therefore, is proposing a new approach to optimizing biventricular pacing, implementing an analysis of endocardial acceleration, more precisely the analysis of peaks of endocardial acceleration.

Indeed, the clinical studies that have been carried out show that endocardial acceleration is a parameter that allows one to obtain very exhaustive information on the functional status of myocardium, either in the case of a normal behavior or deficient behavior: the endocardial acceleration, measured by an accelerometer in direct contact with the heart muscle (generally, but not exclusively, level with the right ventricular apex), indeed very accurately reflects, in real time, the phenomenon concurrent to the mechanical behavior of the heart.

More precisely, European Patent EP-0 515 319 and its counterpart U.S. Pat. No. 5,304,208 (assigned to Sorin Biomedica Cardio SpA), which are incorporated herein by reference, disclose a technique to collect a signal representing endocardial acceleration by means of an endocardial lead with a distal pacing electrode placed at the fundus of the ventricle and equipped with a micro-accelerometer allowing to measure endocardial acceleration. The endocardial acceleration signal thus collected over one cardiac cycle notably comprises two peaks, corresponding to the two major noises that are likely to be heard for each cycle of a normal healthy heart:

The first peak of endocardial acceleration ("PEA I") corresponds to the closure of mitral and tricuspid valves, at the beginning of the phase of isovolumetric ventricular contraction (systole). The variations of this first peak are closely related to pressure variations in the ventricle (the amplitude of PEA peak, being more precisely correlated to the positive maximum of pressure variation, dP/dt, in the left ventricle) and can therefore constitute a representative parameter for myocardium contractility, being itself correlated to the level of activity of the sympathetic system.

the second peak of endocardial acceleration ("PEA II") corresponds to the closure of aortic and pulmonary valves, during the phase of isovolumetric ventricular relaxation. That second peak, which is produced by the brutal deceleration of moving blood mass in the aorta, constitutes a representative parameter for peripheral blood pressure at the beginning of the diastole.

European Patent EP-0 655 260 and its counterpart U.S. Pat. No. 5,396,351 assigned to Sorin Biomedica Cardio SpA and incorporated herein by reference disclose a technique to process the signal of endocardial acceleration delivered by the sensor at the tip of the lead, so as to derive therefrom, two respective values related to these peaks of endocardial acceleration, notably useful for the detection of heart disorders, and potential triggering of a defibrillation therapy.

The device of the invention is belonging to the type described in EP-1 108 446 and U.S. Pat. No. 6,566,866 referred to above, i.e. comprises means for collecting a signal representing endocardial acceleration and means for analyzing the signal, able to determine at least one peak value that is function of one and/or the other of the two peaks of endocardial acceleration over a given cycle, these two peaks corresponding to a first peak during the isovolumetric ventricular contraction phase and a second peak during the isovolumetric ventricular relaxation phase.

In accordance with the present invention, the device also include means for helping to search for an optimal pacing configuration, such means further comprising assessing means, able to determine, for each pacing configuration, a respective performance index, that is derived from the peak value(s).

In a preferred embodiment of the invention, the means for helping to search for an optimal pacing configuration further comprise scanning means, able to vary, in a controlled manner, a functional parameter of the device, and the assessing means are means able to derive the performance index, based upon the successive values taken by the peak value(s) throughout the variation of the functional parameter. The functional parameter is preferably the atrio-ventricular delay, separating a spontaneous or paced ventricular event subsequent to an atrial pacing pulse. The assessing means are means able to derive the performance index based upon the surface area defined below the characteristic of the peak value (s) as a function of this functional parameter.

Advantageously, as an alternative or addition to the embodiment described above, said peak value is a value selected from among the group comprising: the first peak amplitude, the first peak duration, the time interval between the first peak and the consecutive second peak, the time interval between the second peak and the consecutive first peak, and a combination of these values. In yet another embodiment, the device optionally incorporates means able to modify the pacing configuration, to evaluate for a plurality of different configurations, and identify the configuration providing the highest performance index, and to parameterize the device based upon the latter configuration. Preferably, the means able to modify the pacing configuration further comprise means for selecting pacing sites and/or modifying the sequence of delivery of the pacing pulses to the different pacing sites, and/or modifying the time interval(s) separating the delivery of pacing pulses to the different pacing sites.

BRIEF DESCRIPTION OF THE DRAWINGS

Further features, advantages and characteristics of the present invention will now be described with reference to the following detailed discussion of a preferred embodiment of the present invention, made with reference to the attached drawings, in which.

DETAILED DESCRIPTION OF THE INVENTION

One will now describe a preferred embodiment of the present invention. Preliminarily, regarding the software-related aspects thereof, the invention can be implemented by means of an appropriate programming of the software of a known active implantable device, for example, of a triple or quadruple-chamber pacemaker type device comprising a ventricular resynchronization mode. The invention can notably be applied to the implantable devices marketed by ELA Medical, Montrouge, France, such as the Symphony and Rhapsody brand pacemakers. These devices are equipped with programmable microprocessors, including circuits intended to acquire, format and process electrical signals collected by implanted electrodes, and deliver pacing pulses to these electrodes. It is also possible to upload towards these devices, by telemetry, software routines that will be stored in internal memory and run so as to implement the features of the invention, described in more details below. Implementing the features of the invention into these devices is easily feasible by a person of ordinary skill in the art, and will therefore not be described in detail herein.

Figure 1:
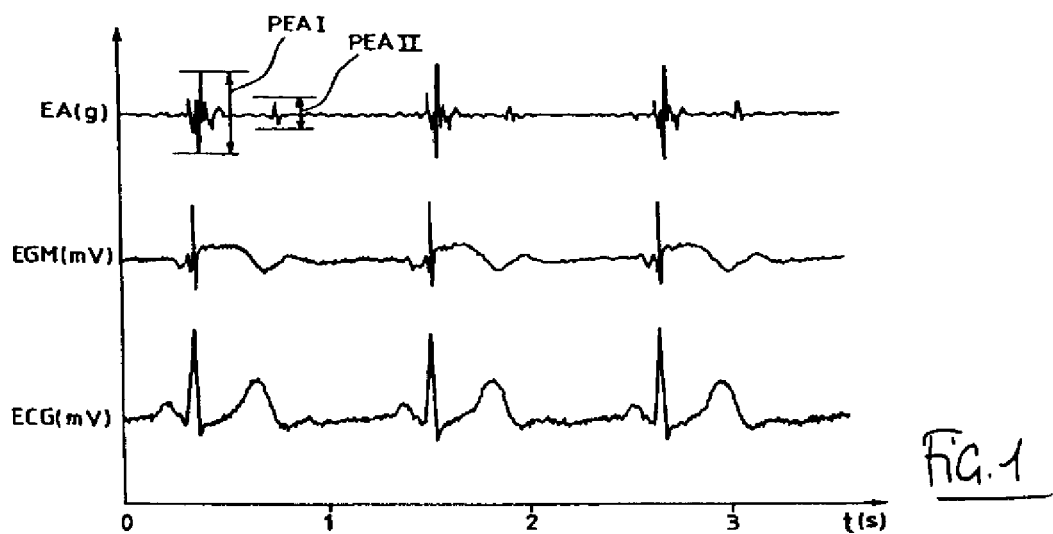
FIG. 1 is a time diagram showing, throughout three successive cardiac cycles, variations of the endocardial acceleration as well as the electrogram and surface electrocardiogram.

The curve at the top of FIG. 1 represents the variations of endocardial acceleration (EA), measured by a sensor such as that described in EP-0 515 319 and U.S. Pat. No. 5,304,208 referred to below, the disclosure of which is hereby incorporated herein by reference, embedded within the distal tip of an endocardial lead placed at the fundus of the ventricle. This figure also illustrates electrogram (EGM) records, i.e., records of the electrical signal collected by the distal electrode of this sensor in mV; and the corresponding surface electrocardiogram (ECG) record, also in mV, over three consecutive heart cycles. As explained above, the acceleration record presents two successive complexes, or endocardial acceleration peaks (PEA), the amplitude and duration of which can be determined by an appropriate processing of the signal delivered by the acceleration sensor, as described in EP-A-0 655 260 and U.S. Pat. No. 5,396,315 referred to above, the disclosure of which is hereby incorporated herein by reference. One will hereinafter refer to "peak amplitude" when referring to the maximum peak to peak value of the acceleration signal separating the two extrema, positive and negative, corresponding to the variances PEA I and PEA II shown on the time diagram of FIG. 1. One will hereinafter refer to "peak duration" when referring to the time interval between the beginning and the end of this complex.

The invention is proposing to utilize the parameters relating to endocardial acceleration collected by the means described above, so as to determine an optimal pacing configuration for the patient, at the time of implantation and also thereafter. Various parameters may be used to that end, notably, are: the amplitude of PEA I and/or PEA II, the duration of PEA I and/or PEA II, the time interval separating PEA I from the consecutive associated PEA II, the time interval separating PEA II from the consecutive PEA I of the following heart cycle, and combinations of the foregoing.

In a first embodiment of the invention, the physician is using the amplitude of PEA I as a guide during the implantation procedure. The sequence of operations is then as follows:
a) implantation of atrial and right ventricular leads (the right ventricular lead being equipped with an embedded accelerometer);
b) positioning of left ventricular lead at an appropriate site;
c) hooking up of generator and application of a short sequence of pacing pulses;
d) recording of PEA I amplitude during pacing;
e) reiteration of steps b) to d) while modifying each time the position (pacing site) of left ventricular lead;
f) choosing the position that provides a maximum PEA I amplitude.

In an alternative embodiment, step d) of the PEA I amplitude recording can be completed or replaced by recording one or more other parameters, for instance measurement of the amplitude and duration of PEA I, or measurement of the amplitude and/or duration of PEA II and the interval PEA I to PEA II (an interval that is representative of the ejection duration). When several parameters are combined together, a combined performance index is calculated based upon the different measurements, so as to allow evaluation of the tested configuration, the final choice being that of the configuration which provides the maximum value for the performance index.

Thus, is it possible to use a performance index that is, for example (in a non-limiting manner), calculated by the following formula:

$$\text{Index} = \text{amplitude}_{PEA\ I} * [\text{interval PEA I-PEA II}]/\text{duration}_{PEA\ I}$$

Evaluation of the performance index can be performed cycle by cycle, in real-time during displacement of left ventricular electrode though different pacing sites. Placing of right ventricular lead and/or the pacing sequence may also be modified.

The choice of pacing sites is, in principle, not modifiable after the implantation. However, some devices are equipped with leads, notably bipolar leads, comprising several electrodes within the same cardiac cavity (chamber). It is therefore possible to modify, if need be, the choice of pacing sites through internal commutations of the device, the latter being, for example, of the type described in EP-0 925 806 and its counterpart U.S. Pat. No. 6,253,106 (commonly assigned herewith to ELA Medical), which discloses a multisite device comprising means for selecting electrode configurations, notably able to improve some cardiac parameters such as cardiac output, and which disclosure is incorporated herein by reference. The person of ordinary skill may easily transpose the disclosures of this document to the case of a biventricular pacing device.

Some changes may eventually be made to the pacing sequence after implantation, in an automated manner, or during inspection by a physician, as part of a patient follow-up.

Figure 2:
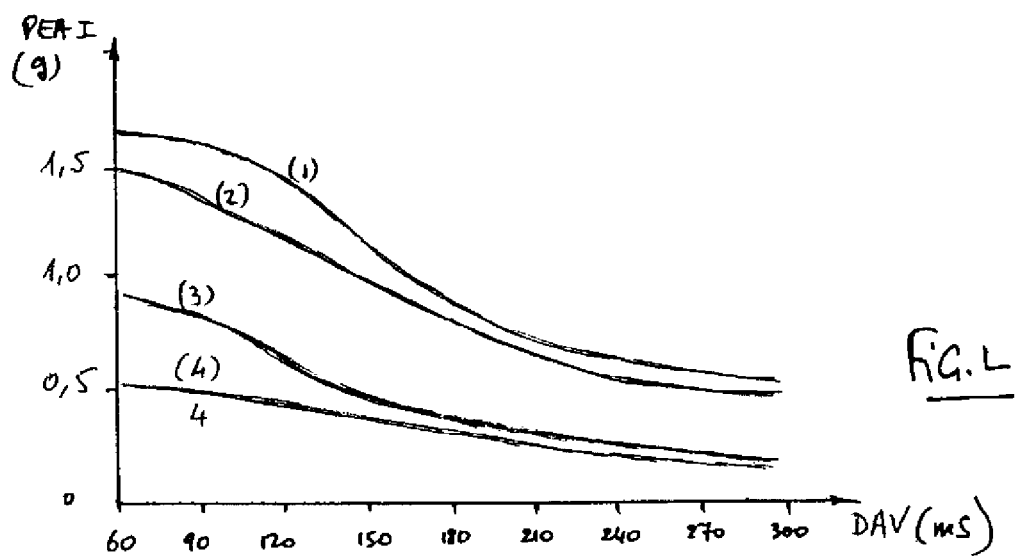
FIG. 2 shows, in representative healthy or sick patients, characteristics of the variation of the amplitude of first endocardial acceleration peak, as a function of atrio-ventricular delay.
Figure 3:
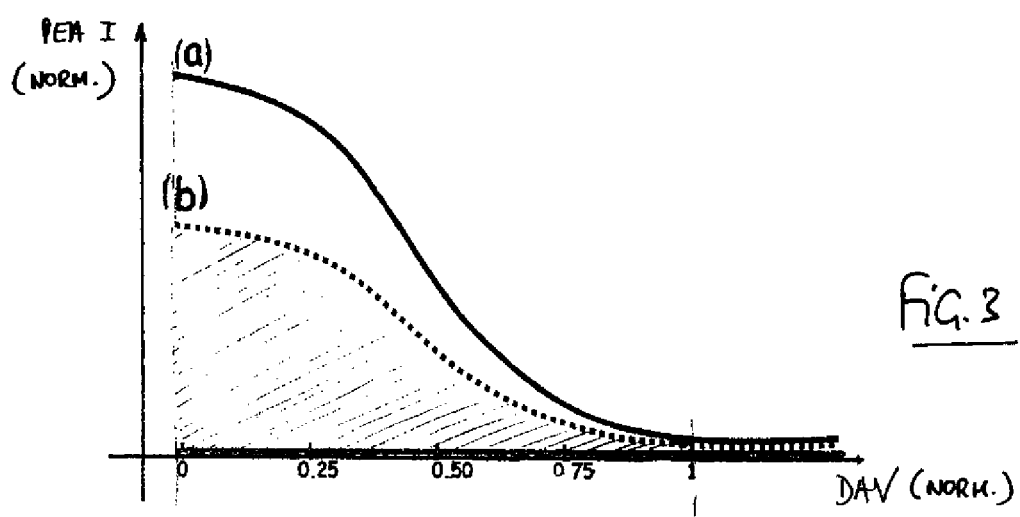
FIG. 3 illustrates a normalized representation of the characteristics illustrated in FIG. 2, for two different pacing configurations.

One will now describe, with reference to FIGS. 2 and 3, another preferred embodiment of the invention, that consists of obtaining, for each pacing configuration, a characteristization of PEA I/AV Delay by carrying out a scanning (i.e., by varying the magnitude of) of the AV Delay while recording the amplitude of PEA I. The reference "DAV" in FIGS. 2 and 3 is to the A-V Delay, measured in mSec.

FIG. 2 shows different characteristics obtained through this method with several patients. In healthy patients, corresponding to the curves disclosed in curves (1) and (2), PEA I amplitude has a characteristic sigmoid shape when the AV Delay is varied between two extrema, typically between 60 and 300 ms. These curves can be interpreted by considering that the decreasing amplitude of PEA I for increasing AV Delays is determined by two main factors, as follows:
the "contractility reserve" of myocardium, corresponding to the level of the baseline (limit value of PEA I for long AV Delays), and
the "noise" produce by the heart valves, mainly the mitral valve, that determine the raising of the amplitude level beyond this baseline, for the shortest AV Delays.

For the second component to be significantly present, it is necessary that the first component be also present, the contractility of myocardium being the "entrainment force" for all the mechanical phenomena that are occurring in the heart over the cardiac cycle. In case of heart failure, when the contractility reserve is marginal, the reduction of ventricular filling for the shortest AV Delays induces a drop of contractility resulting from Frank-Starling Law. For short AV Delays, as it can be seen through curves (3) and (4) in FIG. 2, a raising of PEA amplitude much lower as in healthy patients is obtained, this raising being even not perceptible in some cases.

As a result of the description provided above, in the case of biventricular pacing, an effective pacing configuration is translated into an emphasis of the PEA I/AV Delay characteristic for short AV Delays. A performance index can therefore be established based upon the values taken by the PEA I amplitude for different AV Delays. Advantageously, the performance index can be established based upon the surface area that is underneath this characteristic, which will provide a value that is well representative of the proportion of myocardiac fibers contributing to the systole, therefore providing an increased cardiac contractility measured by the amplitude of PEA I.

FIG. 3 shows through (a) and (b) two PEA I/AV Delay characteristics obtained in a same patient for two different pacing configurations. In order to facilitate the calculations, variation of the AV Delay is preferably normalized from 0 to 1, corresponding to the two extrema of the variation, and an algorithm is determining the area underneath the characteristic obtained while scanning the AV Delay (hatched surface area in FIG. 3). The optimal configuration is defined as that providing the highest surface area value: Thus, in FIG. 3, the configuration corresponding to the characteristic (a) is considered as more effective than that corresponding to the configuration of characteristic (b).

The performance index provided by the surface area value can be utilized, as described above, so as to choose the most appropriate pacing configuration during the implantation procedure and thereafter, either in an automated manner by the device, or under the supervision of a physician during a follow-up visit of the patient. This performance index can be modified so as to include, beside of the surface area parameter A derived from the PEA I/AV Delay characteristic, some other parameters of endocardial acceleration, for example, the duration $d_{REMP}$ of ventricular filling, and/or duration $d_{PEA}$ I of the PEA I complex, in order to provide (in a non-limitative manner) an index calculated as follows:

$$\text{Index} = A * d_{REMP}/d_{PEA\ I}$$

Such a combined index will take higher values with pacing configurations that induce a larger surface area and a longer filling duration, and that also minimize the duration of the PEA I complex.

The performance index may also be determined based upon a mean value of PEA I amplitude, which actually corresponds to the surface area of PEA I/AV Delay characteristic with a variation of AV Delay normalized from 0 to 1.

Some other parameters of endocardial acceleration may also be introduced in this index, such as PEA II amplitude, or the variance between maximum and minimum values taken by PEA I amplitude when the AV Delay is varied over the chosen interval.

Some values other than those relating to endocardial acceleration may also be introduced in the performance index, for example, the heart rate at rest, and/or the level of physical and/or physiological activity of the patient as determined by an activity sensor or a minute ventilation sensor, which measurement techniques are well known in the art.

One skilled in the art will appreciate that the present invention can be practiced by other than the described embodiments, which are presented for purposes of illustration and not of limitation.

We claim:

1. An active implantable medical device with biventricular pacing, comprising:
    means for collecting a signal of endocardial acceleration (EA), wherein the signal of EA over one given cycle comprises a first peak during the isovolumetric ventricular contraction phase (PEA I) and a second peak during the isovolumetric ventricular relaxation (PEA II),
    means for determining a performance value representative of at least one peak of said first peak and said second peak,
    means for providing pacing pulses to a plurality of pacing sites of the device in a plurality of pacing configurations, and
    means for searching for an optimal pacing configuration out of the plurality of pacing configurations, said means for searching further comprising assessing means, able to determine, for each pacing configuration of a plurality of pacing configurations, a performance index,
    wherein the means for searching is able to vary, in a controlled manner, a functional parameter of the device over a predetermined range to derive the performance index based on the successive performance values over the predetermined range.

2. The device of claim 1, wherein
    the performance index is determined by normalizing the functional parameter of the device and the successive performance values over the predetermined range.

3. The device of claim 2, wherein the functional parameter is the atrio-ventricular delay (AV Delay) separating a ventricular event, spontaneous or paced, consecutive to an atrial pacing event.

4. The device of claim 2, wherein the performance index is derived from the value of a surface area defined underneath a characteristic curve of the successive performance values as a function of the functional parameter and wherein the pacing configuration of the plurality of pacing configurations having the largest value of the surface area corresponds to the optimal pacing configuration.

5. The device of claim 1, wherein the performance value is selected from among a group consisting of: the amplitude of the first peak, the duration of the first peak, the time interval between the first peak to the consecutive second peak of the one given cycle, the time interval between the second peak and the consecutive first peak of the following cycle, and a combination of said values.

6. The device of claim 1, further comprising
    means for modifying the pacing configuration, to evaluate among the plurality of pacing configurations, the optimal pacing configuration leading to the highest performance index, and to parameter the device according to that said optimal pacing configuration.

7. The device of claim 6, wherein the means for modifying the pacing configuration further comprises means for selecting a pacing site of the plurality of pacing sites.

8. The device of claim 6, wherein the means for modifying the pacing configuration further comprises means for modifying the sequence of delivery of the pacing pulses to the plurality of pacing sites.

9. The device of claim 6, wherein the means for modifying the pacing configuration further comprises means for modifying the time interval(s) separating the delivery of the pacing pulses between the plurality of pacing sites.

10. An active implantable medical device with biventricular pacing, comprising:
    means for detecting an endocardial acceleration (EA) signal, including a first peak during the isovolumetric ventricular contraction phase (PEA I) and a second peak during the isovolumetric ventricular relaxation (PEA II) of a given cardiac cycle;
    means for analyzing the detected EA signal, able to determine a performance value representative of at least one peak of said first peak and said second peak;
    means for providing pacing pulses to a plurality of pacing sites of the device in a plurality of pacing configurations; and
    means for determining a performance index derived from said performance value for a each pacing configuration of the plurality of pacing configurations, wherein said determined performance index is derived based on the successive performance values over a predetermined range by varying, in a controlled manner, a functional parameter of the device over the predetermined range.

11. The device of claim 10, wherein
    the performance index is determined by normalizing the functional parameter of the device and the successive performance values over the predetermined range.

12. The device of claim 11, wherein the functional parameter further comprises an atrio-ventricular delay (AV Delay) separating a ventricular event, spontaneous or paced, consecutive to an atrial pacing event.

13. The device of claim 10, wherein the performance index is derived from the value of a surface area defined underneath a characteristic curve of the successive performance values as a function of the functional parameter and wherein the pacing configuration of the plurality of pacing configurations having the largest value of the surface area corresponds to the optimal pacing configuration.

14. The device of claim 10, wherein the performance value is selected from among a group consisting of: the amplitude of the first peak, the duration of the first peak, the time interval between the first peak to the consecutive second peak of the one given cycle, the time interval between the second peak and the consecutive first peak of the following cycle, and a combination of said values.

15. The device of claim 10, further comprising means for modifying the pacing configuration, to evaluate among the plurality of pacing configurations, the optimal pacing configuration corresponding to the highest performance index.

16. The device of claim 15 further comprising means for configuring said device according to the optimal pacing configuration.

17. The device of claim 15, wherein the means for modifying the pacing configuration further comprises means for selecting a pacing site of the plurality of pacing sites.

18. The device of claim 15, wherein the means for modifying the pacing configuration further comprises means for modifying the sequence of delivery of the pacing pulses to the plurality of pacing sites.

19. The device of claim 15, wherein the means for modifying the pacing configuration further comprises means for modifying the time interval(s) separating the delivery of the pacing pulses between plurality of pacing sites.

* * * * *